(12) United States Patent
Horn et al.

(10) Patent No.: US 7,805,818 B2
(45) Date of Patent: Oct. 5, 2010

(54) NONWOVEN LOOP MEMBER FOR A MECHANICAL FASTENER

(75) Inventors: Thomas Alexander Horn, Frankfurt (DE); John Norman Simmons, Fischbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/781,613

(22) Filed: Feb. 18, 2004

(65) Prior Publication Data

US 2004/0158957 A1 Aug. 19, 2004

Related U.S. Application Data

(63) Continuation of application No. PCT/US02/28311, filed on Sep. 5, 2002.

(30) Foreign Application Priority Data

Sep. 5, 2001 (EP) ................................. 01121204

(51) Int. Cl.
*A44B 18/00* (2006.01)
(52) U.S. Cl. .............................. 24/448; 156/356; 428/96
(58) Field of Classification Search .................... 24/442, 24/444, 447, 448; 604/391; 156/290; 428/94, 428/96, 97, 99; 442/408, 409
See application file for complete search history.

(56) References Cited

U.S. PATENT DOCUMENTS 3,577,607 A 5/1971 Ikoma (Continued)

FOREIGN PATENT DOCUMENTS

EP 0 289 198 A1 11/1988

(Continued)

OTHER PUBLICATIONS

International Search Report, PCT/US2005/038278, mailed Mar. 17, 2006.

(Continued)

*Primary Examiner*—Jack W. Lavinder
(74) *Attorney, Agent, or Firm*—Charles R. Ware; Laura L. Whitmer; George H. Leal

(57) ABSTRACT

A loop member for a mechanical fastener comprises a nonwoven web, the nonwoven web having a pattern of intersecting bond lines. The pattern is characterized in that at least a portion comprises a first plurality of non-intersecting continuous bond lines and a second plurality of non-intersecting continuous bond lines, each non-intersecting continuous bond line of the first plurality intersecting each non-intersecting continuous bond line of the second plurality. The intersecting bond lines define unbonded pattern elements, each of the pattern elements being at least partially bounded by non-linear segments of the bond lines. The bond pattern for a nonwoven web is suitable for use as a loop member of a mechanical fastener. The bond pattern comprises intersecting bond lines having a uniform width and defining a number of bond pattern elements per unit area, wherein at least one of the bond lines is nonlinear, and wherein the ratio of contour to overall bonded area of the bond pattern is greater than a bond pattern comprising all straight lines having the same uniform line width and defining the same number of bond pattern elements per unit area.

8 Claims, 6 Drawing Sheets

U.S. PATENT DOCUMENTS

| | | | |
|---|---|---|---|
| 3,687,754 A * | 8/1972 | Stumpf | 156/72 |
| 3,694,867 A | 10/1972 | Stumpf | |
| 3,708,361 A | 1/1973 | Stumpf | |
| 3,860,003 A | 1/1975 | Buell | |
| 3,913,183 A | 10/1975 | Brumlik | |
| 3,943,981 A | 3/1976 | De Brabander | |
| 3,959,051 A | 5/1976 | Schirmer | |
| 4,381,781 A | 5/1983 | Sciaraffa et al. | |
| 4,446,189 A * | 5/1984 | Romanek | 428/152 |
| 4,515,595 A | 5/1985 | Kievit et al. | |
| 4,600,618 A | 7/1986 | Raychok, Jr. | |
| 4,662,037 A | 5/1987 | Provost | |
| 4,695,278 A | 9/1987 | Lawson | |
| 4,710,189 A | 12/1987 | Lash | |
| 4,720,415 A | 1/1988 | Vander Wielen | |
| 4,725,473 A | 2/1988 | Van Gompel | |
| 4,761,322 A | 8/1988 | Raley | |
| 4,795,454 A | 1/1989 | Dragoo | |
| 4,808,178 A | 2/1989 | Aziz et al. | |
| 4,816,025 A | 3/1989 | Foreman | |
| 4,846,815 A | 7/1989 | Scripps | |
| 4,857,067 A | 8/1989 | Wood et al. | |
| 4,891,258 A | 1/1990 | Fahrenkrug | |
| 4,909,803 A | 3/1990 | Aziz et al. | |
| 4,920,617 A | 5/1990 | Higashinaka | |
| 4,938,753 A | 7/1990 | Van Gompel et al. | |
| 4,940,464 A | 7/1990 | VanGompel et al. | |
| 4,973,326 A | 11/1990 | Wood | |
| 5,026,364 A | 6/1991 | Robertson | |
| 5,032,122 A | 7/1991 | Noel | |
| 5,058,247 A | 10/1991 | Thomas et al. | |
| 5,092,861 A | 3/1992 | Nomura et al. | |
| 5,098,522 A | 3/1992 | Smurkoski et al. | |
| 5,133,112 A | 7/1992 | Gomez-Acevedo | |
| 5,151,092 A | 9/1992 | Buell | |
| 5,221,274 A | 6/1993 | Buell | |
| 5,246,433 A | 9/1993 | Hasse et al. | |
| 5,326,612 A | 7/1994 | Goulait | |
| 5,380,313 A | 1/1995 | Goulait | |
| 5,407,439 A | 4/1995 | Gulait | |
| 5,470,417 A | 11/1995 | Goulait | |
| 5,476,702 A | 12/1995 | Datta | |
| 5,518,801 A | 5/1996 | Chappell et al. | |
| 5,547,531 A | 8/1996 | Allen | |
| 5,554,145 A | 9/1996 | Roe et al. | |
| 5,569,233 A | 10/1996 | Goulait | |
| 5,569,234 A | 10/1996 | Buell et al. | |
| 5,571,096 A | 11/1996 | Dobrin et al. | |
| 5,580,411 A | 12/1996 | Nease et al. | |
| 5,586,371 A | 12/1996 | Thomas | |
| 5,595,567 A * | 1/1997 | King et al. | 604/391 |
| 5,605,729 A | 2/1997 | Mody | |
| 5,607,537 A | 3/1997 | Johnson et al. | |
| 5,607,760 A | 3/1997 | Roe | |
| 5,609,587 A | 3/1997 | Roe | |
| 5,614,281 A | 3/1997 | Jackson | |
| 5,615,460 A | 4/1997 | Weirich | |
| 5,624,427 A | 4/1997 | Bergman | |
| 5,635,191 A | 6/1997 | Roe et al. | |
| 5,643,397 A | 7/1997 | Gorman | |
| 5,643,588 A | 7/1997 | Roe et al. | |
| 5,647,864 A | 7/1997 | Allen | |
| 5,660,918 A | 8/1997 | Dutta | |
| 5,662,638 A | 9/1997 | Johnson | |
| 5,669,897 A | 9/1997 | LaVon et al. | |
| 5,685,874 A | 11/1997 | Buell et al. | |
| 5,699,593 A | 12/1997 | Jackson | |
| 5,707,707 A | 1/1998 | Burnes | |
| 5,716,470 A | 2/1998 | Belau | |
| 5,736,214 A | 4/1998 | Billarant | |
| 5,763,041 A | 6/1998 | Leak | |
| 5,773,120 A | 6/1998 | Deka | |
| 5,797,896 A | 8/1998 | Schmitz | |
| 5,814,190 A | 9/1998 | Van Phan | |
| 5,830,298 A | 11/1998 | Jackson | |
| 5,830,558 A | 11/1998 | Barnholtz | |
| 5,853,404 A | 12/1998 | Schmitz | |
| 5,855,991 A | 1/1999 | McLarty, III | |
| 5,858,515 A | 1/1999 | Stokes et al. | |
| 5,865,823 A | 2/1999 | Curro | |
| 5,876,532 A | 3/1999 | Billarant | |
| 5,888,607 A | 3/1999 | Seth | |
| 5,897,545 A | 4/1999 | Kline et al. | |
| 5,921,977 A | 7/1999 | Schmitz | |
| 5,925,027 A | 7/1999 | Schmitz | |
| 5,957,908 A | 9/1999 | Kline et al. | |
| 5,964,742 A | 10/1999 | McCormack et al. | |
| 5,997,981 A | 12/1999 | Mccormack | |
| 6,004,306 A | 12/1999 | Robles et al. | |
| 6,027,485 A | 2/2000 | Matsushita | |
| 6,120,487 A | 9/2000 | Ashton | |
| 6,120,489 A | 9/2000 | Johnson et al. | |
| 6,146,738 A | 11/2000 | Tsuji | |
| 6,162,522 A | 12/2000 | Deka | |
| H1952 H | 3/2001 | Reed | |
| 6,196,031 B1 | 3/2001 | Ducauchuis | |
| 6,358,594 B1 | 3/2002 | Ampulski | |
| 6,576,091 B1 | 6/2003 | Cabell et al. | |
| 7,262,335 B2 | 8/2007 | Motsch et al. | |
| 2002/0187696 A1 | 12/2002 | Veiga et al. | |
| 2004/0158957 A1 | 8/2004 | Horn et al. | |
| 2006/0080810 A1 | 4/2006 | Horn et al. | |

FOREIGN PATENT DOCUMENTS

| | | |
|---|---|---|
| EP | 0 341 993 A1 | 11/1989 |
| EP | 0 381 087 A1 | 8/1990 |
| EP | 0 583 031 A2 | 2/1994 |
| EP | 0 583 081 A1 | 2/1994 |
| EP | 0 604 731 A1 | 7/1994 |
| EP | 0 844 062 A1 | 5/1998 |
| EP | 0 882 828 A1 | 12/1998 |
| EP | 0 913 104 A2 | 5/1999 |
| EP | 0 882 828 B1 | 3/2003 |
| EP | 1048236 B1 | 10/2004 |
| JP | 09-279467 A | 10/1997 |
| JP | 09-279467 A1 | 10/1997 |
| WO | WO 94/08789 A1 | 4/1994 |
| WO | WO 95/12702 A1 | 5/1995 |
| WO | WO 95/16746 A1 | 6/1995 |
| WO | WO 95/17111 A1 | 6/1995 |
| WO | WO 95/25496 A2 | 9/1995 |
| WO | WO 95/33390 A1 | 12/1995 |
| WO | WO 96/14459 A1 | 5/1996 |
| WO | WO 97/19665 A1 | 6/1997 |
| WO | WO 97/23348 A2 | 7/1997 |
| WO | WO 99/14045 A1 | 3/1999 |
| WO | WO 99/14046 A1 | 3/1999 |
| WO | WO 99/65352 A1 | 12/1999 |
| WO | WO 00/57742 A1 | 10/2000 |

OTHER PUBLICATIONS

International Search Report, PCT/02/28311, mailed Apr. 2, 2003.
U.S. Appl. No. 10/967,730, filed Oct. 18, 2004, Office Action dated Jun. 2, 2006.
U.S. Appl. No. 10/967,730, filed Oct. 18, 2004, Response to Office Action dated Sep. 2, 2006.
U.S. Appl. No. 10/967,730, filed Oct. 18, 2004, Office Action dated Nov. 28, 2006.
U.S. Appl. No. 10/967,730, filed Oct. 18, 2004, Amendment with submission of RCE dated May 23, 2008.
U.S. Appl. No. 10/967,730, filed Oct. 18, 2004, Office Action dated Jul. 25, 2008.

U.S. Appl. No. 10/967,730, filed Oct. 18, 2004, Response to Office Action dated Jan. 26, 2009.
U.S. Appl. No. 10/967,730, filed Oct. 18, 2004, Office Action dated Apr. 30, 2009.

U.S. Appl. No. 10/967,730, filed Oct. 18, 2004, Examiner's Answer to Appeal Brief dated Dec. 10, 2007.

* cited by examiner

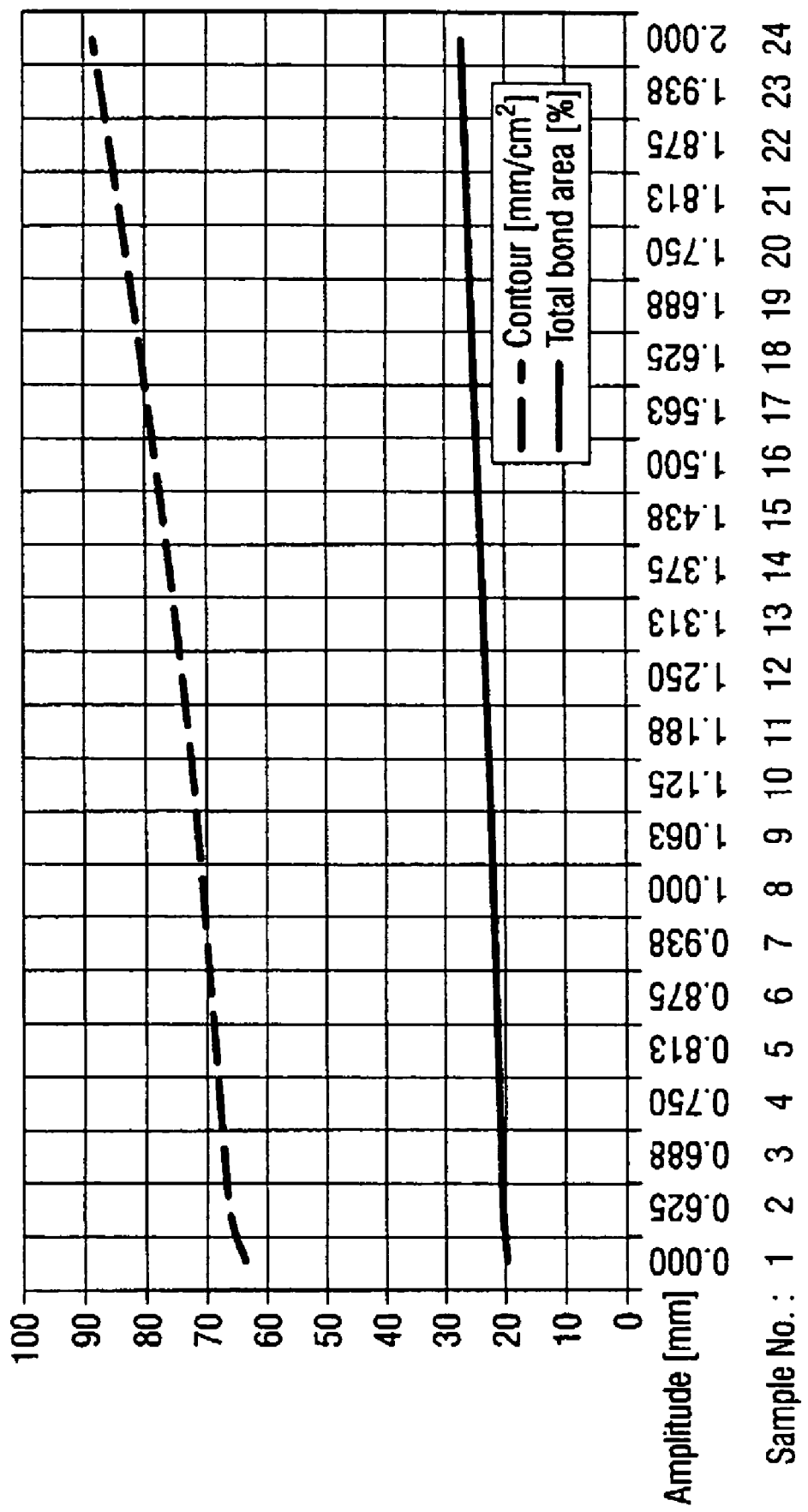

NONWOVEN LOOP MEMBER FOR A MECHANICAL FASTENER

CROSS REFERENCE TO RELATED APPLICATION

This application is a continuation application of prior copending International Application No. PCT/US02/28311 filed Sep. 5, 2002, designating the U.S.

FIELD OF THE INVENTION

This invention relates to mechanical fasteners, often referred to as "hook and loop" fasteners. In particular this invention relates to the loop component of such fasteners.

BACKGROUND OF THE INVENTION

Mechanical fasteners are known in the art. Such fasteners are often called "hook and loop" fasteners. One popular type of mechanical fastener is sold under the trade name Velcro®. Mechanical fasteners permit repeated fastening and unfastening of components having the fastener. In practice, one portion of the component to be fastened has the "hook" members, referred to as the "male" fastener component. Another portion of the component to be fastened has a mating "loop" member, referred to as the "female" fastener component. The hooks and loops are flexible and resilient, such that when pressed together the hooks of the male fastener component engage the loops of the female fastener component in a manner that provides for a certain resistance to release by shear and/or peel forces. The actual amount of resistance depends on a variety of design factors, such as type of loop material, type of hook material, number of hooks (e.g., per unit area), number of loops available for catching by hooks, and the like.

Mechanical fasteners find use in a wide variety of articles, including clothing, sports equipment, industrial equipment, consumer goods, and virtually any item that benefits from repeated opening and closing. One example of clothing, for example, is shoes, where mechanical fasteners often replace shoelaces as a means for secure closure. Mechanical fasteners are also used on disposable articles, such as packaging, medical gowns and disposable diapers as a means for providing for repeated opening and closing.

Much effort has been expended in an effort to provide a more consumer-acceptable mechanical fastener. Consumer acceptability depends on the end use, but in general consumer acceptance for disposable articles can be improved by reducing the cost of the fastener and increasing its reliability. However, a technical contradiction exists between such cost reduction and the desire to increase reliability. For example, woven, knit, and nonwoven webs are known materials useful for female fastening components. Woven and knit materials can be made to provide relatively high reliability due to the ability to make effective loop structures but are relatively high cost materials. Nonwoven materials are significantly less costly to produce, but exhibit significantly less reliability for use as the loop portion of a mechanical fastening member. That is, in general, even with optimized mating hook portions, nonwoven web loop materials exhibit less resistance to peel and shear forces than those exhibited by woven or knit loop materials, and thereby exhibit relatively less reliability as a fastener.

One reason nonwoven webs are less reliable than woven or knit materials as a hook component of a mechanical fastener is the lack of integrity of the "loops" in a nonwoven, that is, the fiber portions available for engaging with a hook member. In a woven or knit material each loop is substantially anchored to resist pulling apart when a mating hook member is disengaged. However, for nonwoven webs, the loops formed by randomly distributed fibers are not necessarily anchored to resist such pulling apart. Therefore, upon disengaging of a hook member, the hook tends to pull fibers loose. The ease with which the fibers can be pulled loose is one factor in determining the peel and shear forces necessary to unfasten the fastener. The number of fibers that get pulled loose is also a factor in determining whether the fastener can be used repeatedly. This problem is especially significant for low basis weight nonwoven webs.

One way to improve the integrity of a nonwoven web is to increase the amount of bonding of the constituent fibers. For example, a nonwoven web can be bonded to a backing layer in known ways, such that constituent fibers are bonded, or anchored to the backing layer. By increasing the bond area, more fibers can be anchored to the backing. However, increasing the bond area also increases the number of fibers that are not available for hook engagement. At 100% bond coverage, for example, each fiber would be anchored to avoid pulling away from the web, but there would be no fibers available for hook engagement.

Attempts have been made to make hook members that are less costly and work well with nonwoven web loop members. For example, U.S. Pat. No. 5,058,247, issued Oct. 22, 1991 to Thomas et al., teaches engaging means in the form of hook-shaped tine for securing in engaging means having strands and fibers. However, there is no teaching in Thomas et al. directed to the optimization of the engaging means, such as a nonwoven web loop member.

Attempts to optimize the nonwoven web loop member have also been made. For example, U.S. Pat. No. 5,595,567 teaches utilizing predetermined patterns of bonding pattern elements on the nonwoven that intersect predetermined construction bonds that join the nonwoven to an elongatable backing. However, this structure requires an elongatable backing, which must have a relaxed orientation, such as an elastomeric material, for example. Therefore, while reliability may be increased, cost is not sufficiently decreased for many applications of disposable articles.

Accordingly, it would be desirable to have a nonwoven loop member for a mechanical fastener with increased fastening reliability.

Additionally, it would be desirable to have a nonwoven loop member for a mechanical fastener with increased fastening reliability that can be made in a commercially viable manner.

Further, it would be desirable to have a nonwoven loop member for a mechanical fastener with increased fastening reliability that does not require a backing material having relaxed orientation.

Finally, it would be desirable to devise a nonwoven loop material for a mechanical fastener having a bond pattern that bonds relatively more fibers without a corresponding significantly increased bond area.

BRIEF SUMMARY OF THE INVENTION

A loop member for a mechanical fastener comprises a nonwoven web, the nonwoven web having a pattern of intersecting bond lines. The pattern is characterized in that at least a portion comprises a first plurality of non-intersecting continuous bond lines and a second plurality of non-intersecting continuous bond lines, each non-intersecting continuous bond line of the first plurality intersecting each non-intersecting continuous bond line of the second plurality. The intersecting bond lines define unbonded pattern elements, each of the pattern elements being at least partially bounded by nonlinear segments of the bond lines.

The bond pattern for a nonwoven web is suitable for use as a loop member of a mechanical fastener. The bond pattern comprises intersecting bond lines having a uniform width and defining a number of bond pattern elements per unit area, wherein at least one of the bond lines is nonlinear, and wherein the ratio of contour to overall bonded area of the bond pattern is greater than a bond pattern comprising all straight lines having the same uniform line width and defining the same number of bond pattern elements per unit area.

BRIEF DESCRIPTION OF THE DRAWINGS

While the specification concludes with claims pointing out and distinctly claiming the present invention, it is believed the same will be better understood by the following drawings taken in conjunction with the accompanying specification wherein like components are given the same reference number.

FIG. 8 is a graph of the data shown in Table 1.

DETAILED DESCRIPTION OF THE INVENTION

Figure 1:
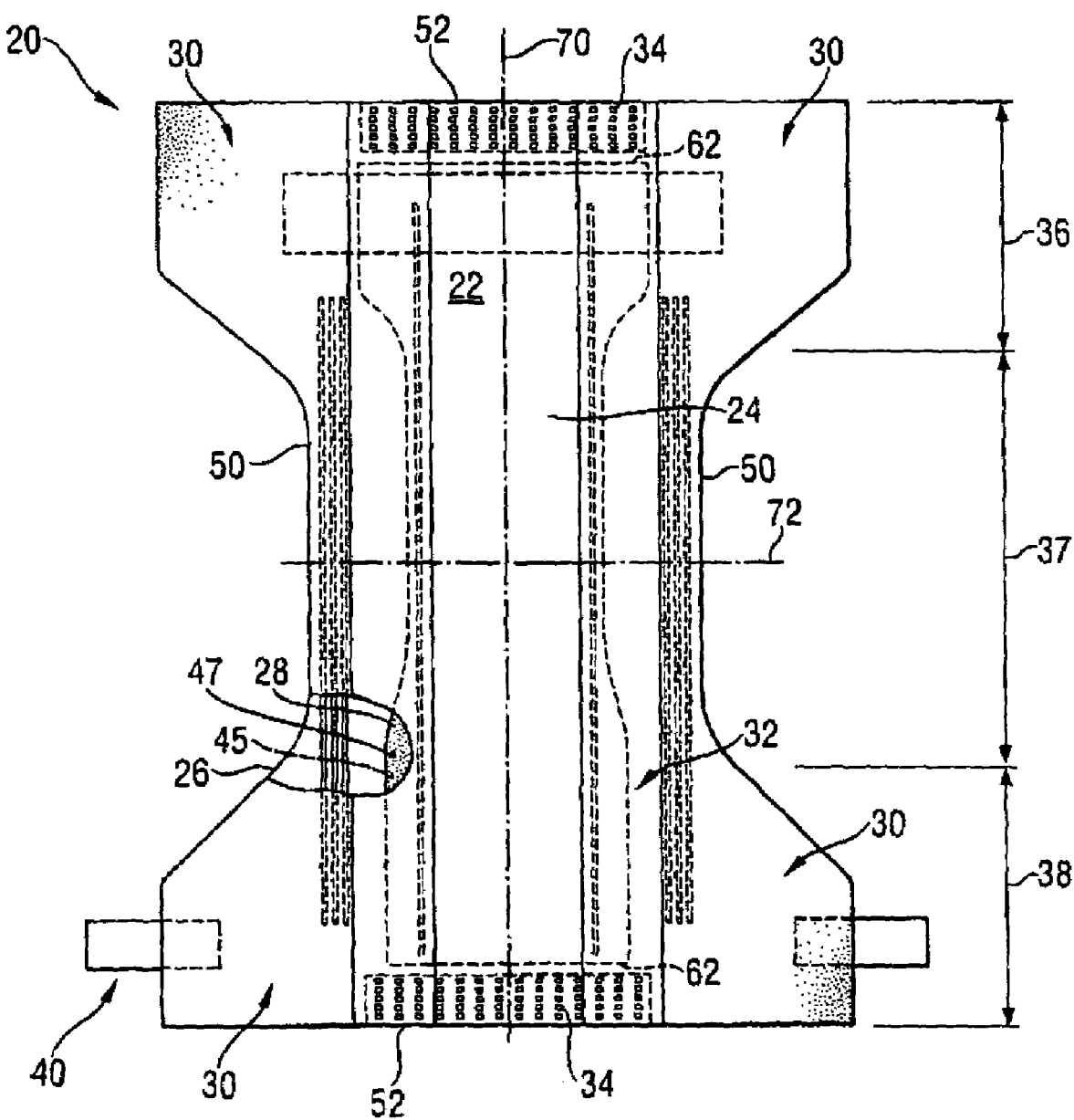
FIG. 1 is a perspective view of one embodiment of an absorbent article of the present invention.

As used herein, the term "absorbent article" refers to devices that absorb and contain body exudates, and more specifically, refers to devices that are placed against or in proximity to the body of the wearer to absorb and contain the various exudates discharged from the body. The term "disposable" is used herein to describe absorbent articles that generally are not intended to be laundered or otherwise restored or reused as an absorbent article (i.e., they are intended to be discarded after a single use).

As used herein, the term "disposed" is used to mean that an element(s) of the diaper is formed (joined and positioned) in a particular place or position as a unitary structure with other elements of the diaper or as a separate element joined to another element of the diaper. As used herein, the term "joined" encompasses configurations whereby an element is directly secured to another element by affixing the element directly to the other element, and configurations whereby an element is indirectly secured to another element by affixing the element to intermediate member(s) that in turn are affixed to the other element.

A "unitary" absorbent article refers to absorbent articles that are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons about the lower torso, and includes both tape-type diapers (adhesive tapes, hook and loop fasteners, etc.), and pull-on pant-type diapers. The present invention is also applicable to other absorbent articles such as incontinence briefs, incontinence undergarments, absorbent inserts, diaper holders and liners, and the like.

As used herein, the term "elastic" or "elastomeric" refers to any material which, upon application of a biasing force, is stretchable, that is, elongatable, at least about 60 percent (i.e., to a stretched, biased length, which is at least about 160 percent of its relaxed unbiased length), and which, will recover at least 55 percent of its elongation upon release of the stretching, elongation force. A hypothetical example would be a one (1.0) cm sample of a material which is elongatable to at least 1.60 cm, and which, upon being elongated to 1.60 cm and released, will recover to a length of not more than 1.27 cm. Many elastic materials may be elongated by more than 60 percent (i.e., much more than 160 percent of their relaxed length), for example, elongated 100 percent or more, and many of these materials will recover to substantially their initial relaxed length, for example, to within 105 percent of their initial relaxed length, upon release of the stretch force. Such materials are referred to herein as "highly elastic".

As used herein, the term "nonelastic" refers to any material that does not fall within the definition of "elastic" (or "elastomeric") or "highly elastic" above.

As used herein, the term "extensible" refers to any material that, upon application of a biasing force, is elongatable, at least about 50% without offering a significant resistance force (less than 10 g/cm) or experiencing catastrophic failure. Catastrophic failure includes substantial tearing, fracturing, rupturing, or other failure in tension such that, if tested in a standard tensile tester, the failure would result in a sudden significant reduction in measured tensile force. As used herein, the term "highly extensible" refers to any material which, upon application of a biasing force, is elongatable, at least about 70%, more preferably at least about 100%, and even more preferably about 120% without offering a significant resistance force (less than 10 g/cm) or experiencing catastrophic failure.

The loop member of the present invention can be used in application requiring a relatively low cost mechanical fastener component, including clothing and packaging applications. However, it is particularly beneficial for disposable products, and is described below with respect to its use as a fastener for a disposable absorbent article, specifically a diaper.

FIG. 1 is a plan view of a disposable diaper 20 in a flat-out state with portions of the structure being cut away to more clearly show the construction of the diaper 20. The portion of the diaper 20 that faces the wearer is oriented towards the viewer. As shown in FIG. 1, the diaper 20 preferably comprises a liquid pervious topsheet 24; a liquid impervious backsheet 26, an absorbent core 28 which is preferably positioned between at least a portion of the topsheet 24 and the backsheet 26; side panels 30; elasticized leg cuffs 32; and an elastic waist feature 34.

Diaper 20 is shown in FIG. 1 to have a first waist region 36, a second waist region 38 opposed to the first waist region 36 and a crotch region 37 located between the first waist region and the second waist region 38. The periphery of the diaper 20 is defined by the outer edges of the diaper 20 in which the longitudinal edges 50 are oriented generally parallel to the longitudinal centerline 70 of the diaper 20 and the end edges 52 run between the longitudinal edges 50 generally parallel to the transverse centerline 72 of the diaper 20. However, for better fit, longitudinal edges 50 are preferably curved to produce an "hourglass" shape diaper when viewed in the flat-out configuration of FIG. 1. The chassis 22 of the diaper 20 comprises the main body of the diaper 20. The chassis 22 comprises at least the topsheet 24 and the backsheet 26.

For tape-type diapers, that is, diapers intended to be fastened about the wearer by use of an adhesive tape or releasable mechanical fastener, the diaper 20 can have a fastening system generally designated 40, as is commonly known in the art. Once fastened upon the wearer, portions of longitudinal edge 50 define leg openings. The fastening system 40 can be a mechanical fastener including the loop member of the present invention.

While the topsheet 24, the backsheet 26, and the absorbent core 26 may be assembled in a variety of well-known configurations, preferred tape-diaper configurations are described generally in U.S. Pat. No. 3,860,003 entitled "Contractible Side Portions for Disposable Diaper" which issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" which issued to Roe et al. on Sep. 10, 1996; U.S. Pat. No. 5,569,234 entitled "Disposable Pull-On Pant" which issued to Buell et al. on Oct. 29, 1996; and U.S. Pat. No. 5,580,411 entitled "Zero Scrap Method For Manufacturing Side Panels For Absorbent Articles" which issued to Nease et al. on Dec. 3, 1996. Preferred pant-type diapers and methods for making suitable side seams are disclosed in U.S. Pat. No. 5,569,234 issued to Buell, et al. on Oct. 29, 1996, U.S. Pat. No. 5,607, 537 issued to Johnson et al. on Mar. 4, 1997, U.S. Pat. No. 5,662,638 issued to Johnson et al. on Sep. 2, 1997, and U.S. Pat. No. 5,685,874 issued to Buell et al. on Nov. 11, 1997. Preferable seams are disclosed in European Patent Application No. 96118654.1 titled "Thermal Joining of Webs" filed on Nov. 21, 1996 (Christoph J. Schmitz).

The backsheet 26 is generally that portion of the diaper 20 positioned adjacent the garment facing surface 45 of the absorbent core 28 which prevents the exudates absorbed and contained therein from soiling articles which may contact the diaper 20, such as bedsheets and undergarments. In preferred embodiments, the backsheet 26 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names XI 5306, X10962 and X10964.

Other suitable backsheet materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and micro porous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL® blend P18-3097. Such breathable composite materials are described in greater detail in PCT Application No. WO 95/16746, published on Jun. 22, 1995 in the name of E. I. DuPont and copending U.S. patent application Ser. No. 08/744,487, filed on Nov. 6, 1996 in the name of Curro. Other breathable backsheets including nonwoven webs and apertured formed films are described in U.S. Pat. No. 5,571,096 issued to Dobrin et al. on Nov. 5, 1996.

The backsheet 26, or any portion thereof, may be elastically extensible in one or more directions. In one embodiment, the backsheet 26 may comprise a structural elastic-like film ("SELF") web. A structural elastic-like film web is an extensible material that exhibits an elastic-like behavior in the direction of elongation without the use of added elastic materials. SELF webs suitable for the present invention are more completely described in U.S. Pat. No. 5,518,801 entitled Web Materials Exhibiting Elastic-Like Behavior, which issued to Chappell, et al. on May 21, 1996.

The backsheet 26 may be joined to the topsheet 24, the absorbent core 28 or any other element of the diaper 20 by any attachment means known in the art. For example, hot melt adhesives applied about the portions of the peripheral edges can be sufficient to join the topsheet and backsheet to one another.

The topsheet 24 is preferably positioned adjacent the body surface 47 of the absorbent core 28 and may be joined thereto and/or to the backsheet 26 by any attachment means known in the art. The topsheet 24 is preferably compliant, soft feeling, and non-irritating to the wearer's skin. Further, at least a portion of the topsheet 24 is liquid pervious, permitting liquid to readily penetrate through its thickness. A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers.

Any portion of the topsheet 24 may be coated with a lotion as is known in the art. Examples of suitable lotions include those described in U.S. Pat. No. 5,607,760 entitled "Disposable Absorbent Article Having A Lotioned Topsheet Containing an Emollient and a Polyol Polyester Immobilizing Agent" which issued to Roe on Mar. 4, 1997; U.S. Pat. No. 5,609,587 entitled "Diaper Having A Lotion Topsheet Comprising A Liquid Polyol Polyester Emollient And An Immobilizing Agent" which issued to Roe on Mar. 11, 1997; U.S. Pat. No. 5,635,191 entitled "Diaper Having A Lotioned Topsheet Containing A Polysiloxane Emollient" which issued to Roe et al. on Jun. 3, 1997; and U.S. Pat. No. 5,643,588 entitled "Diaper Having A Lotioned Topsheet" which issued to Roe et al. on Jul. 1, 1997.

The absorbent core 28 may comprise any absorbent material which is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; melt-blown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The diaper 20 can also comprise at least one elastic waist feature 34 that helps to provide improved fit and containment. The elastic waist feature 34 is generally intended to elastically expand and contract to dynamically fit the wearer's waist. The elastic waist feature 34 preferably extends at least longitudinally outwardly from at least one waist edge 62 of the absorbent core 28 and generally forms at least a portion of the end edge 52 of the diaper 20. Disposable diapers are often constructed so as to have two elastic waist features, one positioned in the first waist region 36 and one positioned in the second waist region 38. Further, while the elastic waist feature 34 or any of its constituent elements may comprise one or more separate elements affixed to the diaper 20, the elastic waist feature 34 may be constructed as an extension of other elements of the diaper 20, such as the backsheet 26, the topsheet 24, or both the backsheet 26 and the topsheet 24. The elastic waist feature 34 may be constructed in a number of different configurations including those described in U.S. Pat. No. 4,515,595 issued to Kievit et al. on May 7, 1985; U.S. Pat. No. 4,710,189 issued to Lash on Dec. 1, 1987; U.S. Pat. No. 5,151,092 issued to Buell on Sep. 9, 1992; and U.S. Pat. No. 5,221,274 issued to Buell on Jun. 22, 1993. Other suitable waist configurations may include waistcap features such as those described in U.S. Pat. No. 5,026,364 issued to Robertson on Jun. 25, 1991 and U.S. Pat. No. 4,816,025 issued to Foreman on Mar. 28, 1989.

The diaper 20 can also comprise side panels 30. The side panels 30 may be elastic or extensible to provide a more comfortable and contouring fit by initially conformably fitting the diaper 20 to the wearer and sustaining this fit throughout the time of wear well past when the diaper 20 has been loaded with exudates since the elasticized side panels 30 allow the sides of the diaper 20 to expand and contract. The side panels 30 may be constructed in any suitable configurations as known in the art. Examples of diapers with elasticized side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151,092 issued to Buell on Sep. 9, 1992; and U.S. Pat. No. 5,221,274 issued to Buell on Jun. 22, 1993; U.S. Pat. No. 5,669,897 issued to LaVon, et al. on Sep. 23, 1997 entitled "Absorbent Articles Providing Sustained Dynamic Fit"; U.S. patent application Ser. No. 08/155,048 entitled "Absorbent Article With Multi-Directional Extensible Side Panels" filed Nov. 19, 1993 in the names of Robles, et al.

The diaper 20 preferably further includes leg cuffs 32 which provide improved containment of liquids and other body exudates. Leg cuffs may also be referred to as legbands, side flaps, barrier cuffs, or elastic cuffs. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. on Feb. 28, 1989 and Mar. 20, 1990, respectively, describe disposable diapers having "stand-up" elasticized flaps (barrier cuffs) that improve the containment of the leg regions. U.S. Pat. Nos. 4,695,278 and 4,795,454 issued to Lawson on Sep. 22, 1987 and to Dragoo on Jan. 3, 1989, respectively, describe disposable diapers having dual cuffs, including gasketing cuffs and barrier cuffs.

The fastening system 40 maintains the first waist region 36 and the second waist region 38 in an overlapping configuration so as to provide tension about the circumference of the waist opening of the diaper 20 to hold the diaper 20 on the wearer. The fastening system 40 comprises hook and loop fastening components, including hook fastening material and the loop member 100 of the present invention.

As used herein, the term "hook fastening material" is used to designate a material having engaging elements designed to "hook" into complementary loop elements, such as loop member 100. The hook member is sometimes referred to as a male fastener. It should also be understood that the use of the term "hook" should be non-limiting in the sense that the engaging elements may comprise any shapes as are known in the art so long as they are adapted to engage a complementary mechanical closure element such as a loop fastening material or another hook fastening material. The hook fastening material can mechanically engage fibrous elements of the loop member 100 of the present invention so as to provide a secure closure. A hook fastening material according to the present invention may be manufactured from a wide range of materials. Suitable materials include nylon, polyester, polypropylene, or any combination of these materials, or other materials as are known in the art.

A suitable hook fastening material comprises a number of shaped engaging elements projecting from a backing such as the commercially available material designated "Scotchmate" brand No. FJ3402 available from Minnesota Mining and Manufacturing Company, St. Paul, Minn. Alternatively, the engaging elements may have any shape such as hooks, "T's", mushrooms, or any other shape as are well known in the art. An exemplary hook fastening material is described in U.S. Pat. No. 4,846,815 entitled "Disposable Diaper Having An Improved Fastening Device" issued to Scripps on Jul. 11, 1989. Another hook fastening material comprises an array of prongs formed of thermoplastic material. Hot melt adhesive thermoplastics, in particular polyester and polyamide hot melt adhesives, are particularly well suited for forming the prongs of the hook fastening material. The prongs are preferably manufactured using a modified gravure printing process by printing the thermoplastic material in its molten state onto a substrate in discrete units, severing the material in a manner that allows stretching of a portion of the thermoplastic material prior to severance, and allowing the stretched molten material to "freeze" resulting in prongs. This hook fastening material and methods and apparatus for making such a hook fastening material are more fully detailed in European Patent Application 0 381 087; The Procter & Gamble Company; published Aug. 8, 1990.

Loop member 100 provides a plurality of fibrous elements that engage the engaging elements of a hook fastening material. Loop member 100 of the present invention comprises a nonwoven material. The nonwoven material can be extensible, elastic, or nonelastic. Examples of nonwoven materials suitable for use as a loop member 100 herein are discussed with respect to the materials useful as the topsheet 24 of the diaper 20. In one embodiment, the loop member 100 can formed by, or as part of, the nonwoven material of the topsheet 24 or backsheet 26. In general, suitable nonwoven materials include thermoplastic polymeric fibrous webs such as spunbond nonwonvens, meltblown nonwovens, carded nonwovens, and hydrotangled nonwovens, and combinations of such nonwovens. That is, the benefits of the present invention are not believed to be limited to a particular type of nonwoven. However, the particular nonwoven used can be chosen to optimize the benefits for particular end use requirements, including performance requirements (e.g., peel or shear force) or application requirements (e.g., softness, aesthetics). For example, without being bound by theory, it is believed that a high loft hydroentangled nonwoven, having no consolidation bond sites, can produce a highly reliable loop member of the present invention for use as a landing zone on disposable diapers. Through-air bonded air laid nonwovens, as well as through-air bonded bicomponent fiber nonwovens can also be used to make highly reliable loop members 100.

Pre-bonded, consolidated commercially available nonwovens exhibit improved performance as a loop fastener of a mechanical fastener system when bonded by the pattern of the present invention. In one embodiment, pre-bonded carded nonwovens having a basis weight of 60 grams per square meter (gsm) having a "soft bonding" pattern of approximately 10%-12% area of discrete thermal bonding, as known in the art, has been found beneficial for use in the present invention.

In general the basis weight of the nonwoven used in the present invention can be chosen based on the end use of a mechanical fastener. For disposable absorbent articles, it has been found that nonwovens having a basis weight in the range of 20-100 gsm, more preferably 40-80 gsm, and more preferably 50-60 gsm work well in the present invention. In particular, when used as a landing zone in a disposable diaper, that is, as the loop component of a hook and loop fastener in a disposable diaper, a consolidated carded nonwoven web having a basis weight of 60 gsm has been found to work well, providing for improved hook engagement while also providing for softness and low cost.

Figure 2:
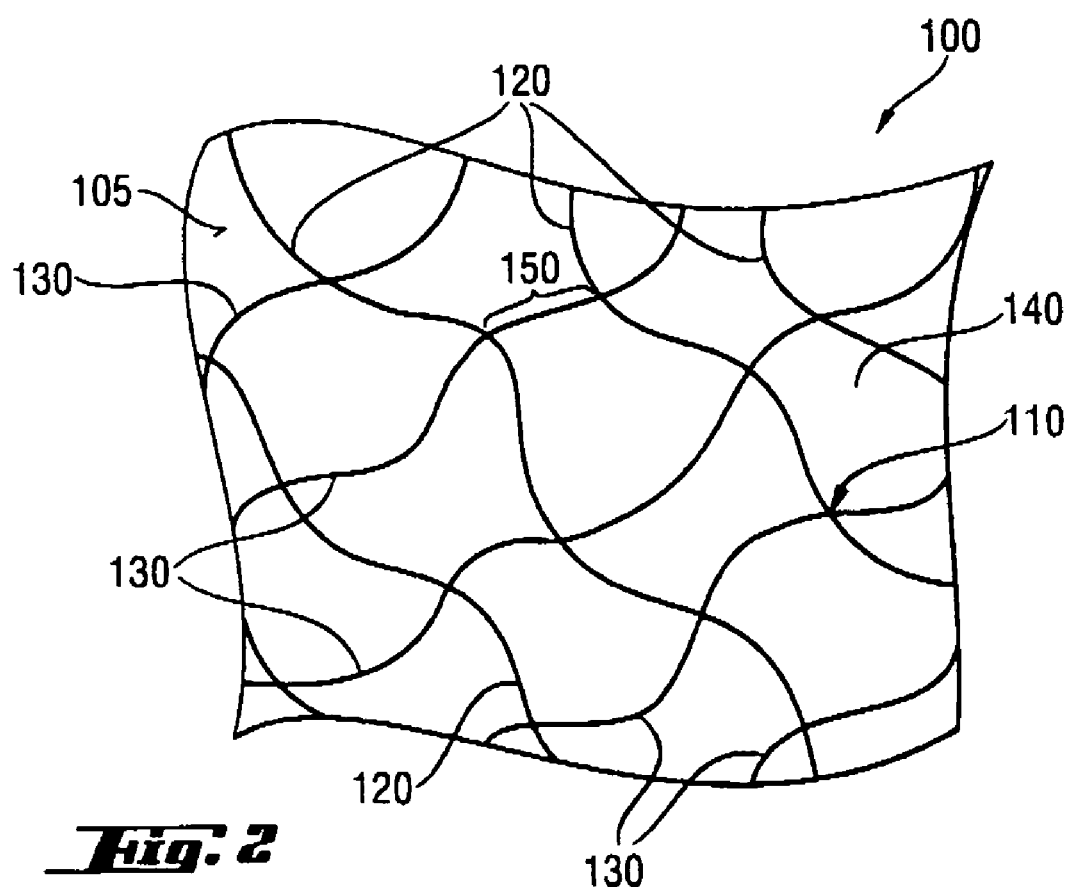
FIG. 2 is a plan view of one embodiment of a loop member of the present invention.

FIG. 2 shows one embodiment of a loop member 100 of the present invention. As shown, a nonwoven web 105 comprises a pattern of intersecting bond lines 110. The pattern of intersecting bond lines 110 serve to anchor the constituent fibers of nonwoven web 105 such that they offer more resistance to being pulled out when subjected to the forces of a mating hook element being disengaged. The pattern of intersecting bond lines 110 also serves to aid in increasing the shear forces required to unfasten a mating hook element by providing for limits on the lateral movement (i.e., parallel to the plane of the page of FIG. 2) of an engaged hook along the hooked fiber(s).

While the pattern of the present invention is disclosed as intersecting bond "lines", it is recognized that the term "line" can also describe a series of discrete points or short lines so closely spaced as to effectively approximate a line. Therefore, those skilled in the art will recognize that, although a solid line bond pattern is necessary to fully realize the benefits of the present invention, the benefits of the present invention can be achieved by sufficiently closely spaced points, or sufficiently long, but broken line segments, that in effect closely approximate in a line.

Furthermore, as used herein, a bond line is preferably a linear construction having a constant width, or line "weight". However, it is recognized that lines having substantially equal widths are sufficient for the benefits of the present invention. Therefore, while a pattern of lines having a constant width are preferred for the present invention, those skilled in the art will recognize that much of the benefit of the present invention can be achieved by the use of lines having a varying width.

Additionally, it is preferred for the present invention that the constant width of individual bond lines be minimized. The minimum width for the bond lines of the present invention depend on the basis weight of the nonwoven material used, and the type of bond line being used. For example, for a 60 gsm basis weight carded nonwoven, having bond lines imparted by a patterned roller in a thermal bond roller arrangement, a minimum line width of about 0.58 mm is preferred. That is, the patterned roller having a raised pattern of lines corresponding to the bond lines, is made such that the raised pattern has a land width of about 0.58 mm, as is known in the art of thermal embossed patterns in nonwoven webs. A land width of less than 0.58 mm is believed to present processing problems, such as cut through of the nonwoven web. For adhesive-bonded bond lines, it is believed that minimum line width is limited only by the processing capability of adhesive application means, and performance requirements of the finished nonwoven. Accordingly, the line width of bond lines of the present invention can be between about 0.20-1.0 mm, preferably about 0.40-0.80 mm, and more preferably between about 0.50-0.60 mm.

Straight intersecting bond lines are known in the art for providing a predetermined amount of bond area to increase the fastening performance of a nonwoven web for use as a loop fastening material. For example, in the aforementioned U.S. Pat. No. 5,595,567, a relatively complex pattern of straight bond lines defining points of intersection is disclosed. As mentioned, one way to increase nonwoven web integrity (i.e., its resistance to constituent fibers from pulling loose) and thereby to increase the reliability of a loop fastening element, is to simply increase the number of straight bond lines in an intersecting pattern. However, doing so correspondingly increases the bond area and consequently decreases the quantity of fibers available for engaging with hook elements. Therefore, the present invention addresses the technical contradiction of how to increase the number of fibers bonded without proportionally increasing the bond area.

Figure 3:
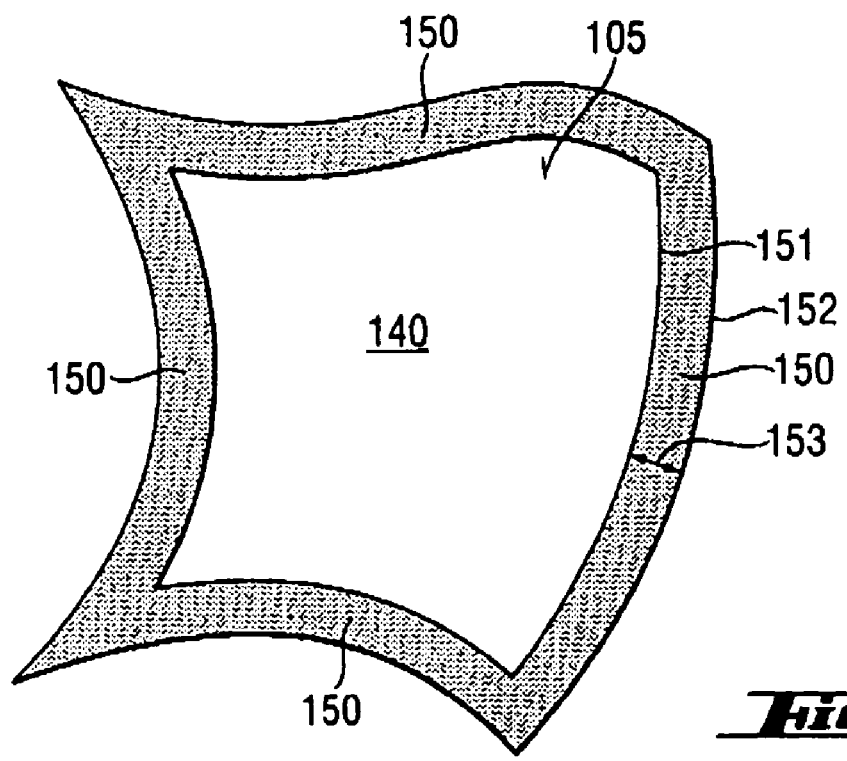
FIG. 3 is plan view showing one representative pattern element of a loop member of the present invention.

The pattern of intersecting bond lines 110 of the present invention comprises non-linear bond lines. With reference to FIG. 2, in one embodiment a first plurality of non-intersecting continuous bond lines 120 and a second plurality of non-intersecting bond lines 130 are combined to form a pattern of intersecting bond lines that define unbonded areas described herein as pattern elements 140, two of which are designated on FIG. 2. Each of the pattern elements 140 is at least partially bounded by non-linear segments 150 of the bond lines 120, 130. One segment 150 is shown in FIG. 2. FIG. 3 shows one pattern element 140 greatly enlarged and bounded by four non-linear segments 150.

Figure 4:
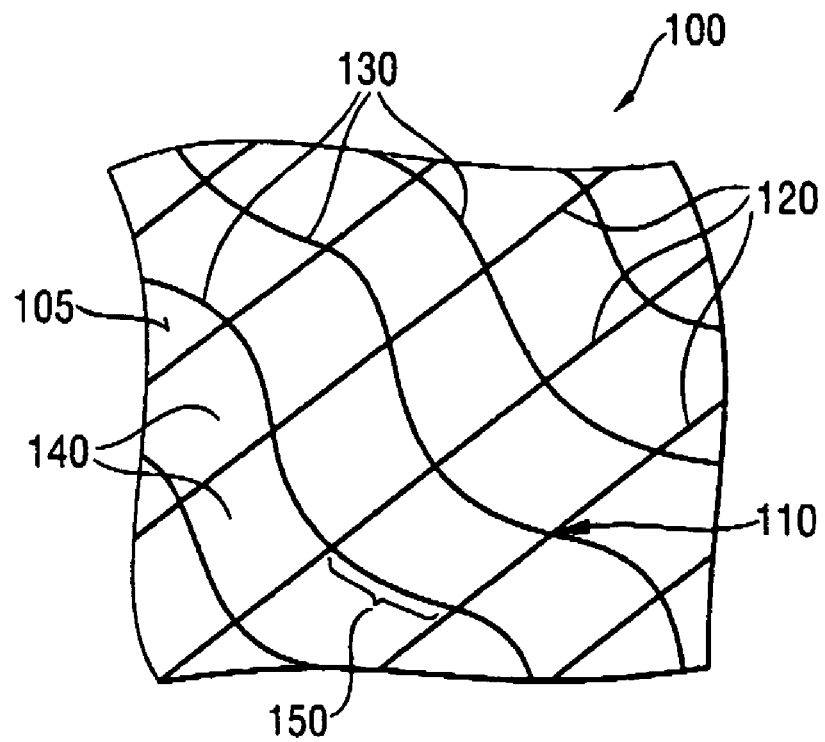
FIG. 4 is a plan view of another embodiment of a loop member of the present invention.

Various modifications can be made to pattern 110. For example, as shown in FIG. 4, first plurality of non-intersecting continuous bond lines 120 can be linear and second plurality of non-intersecting bond lines 130 can be non-linear. When combined to form pattern 110, each of the pattern elements 140 is at least partially bounded by non-linear segments 150 of the bond lines 130. In this embodiment, two linear segments and two non-linear segments bound each pattern element 140.

Figure 5:
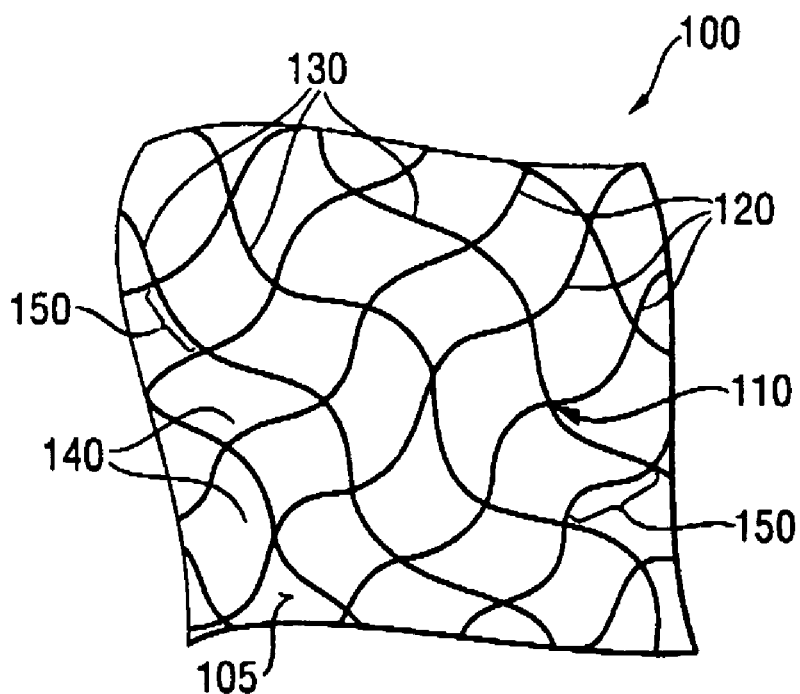
FIG. 5 is a plan view of another embodiment of a loop member of the present invention.

The embodiment shown in FIG. 5 shows each bond line of the first plurality of non-intersecting continuous bond lines 120 can be disposed at a constant equal distance from adjacent bond lines. In FIG. 5 each bond line of the second plurality of non-intersecting bond lines 130 are also disposed at a constant equal distance from adjacent bond lines. That is, as shown in FIG. 5, each bond line in the first or second plurality (120, 130) can be wavy, and "in phase" with adjacent bond lines in the first or second plurality, respectively. In this manner, bond lines within each plurality are non-linear, non-intersecting, and at a constant distance from adjacent bond lines in that plurality.

Figure 6:
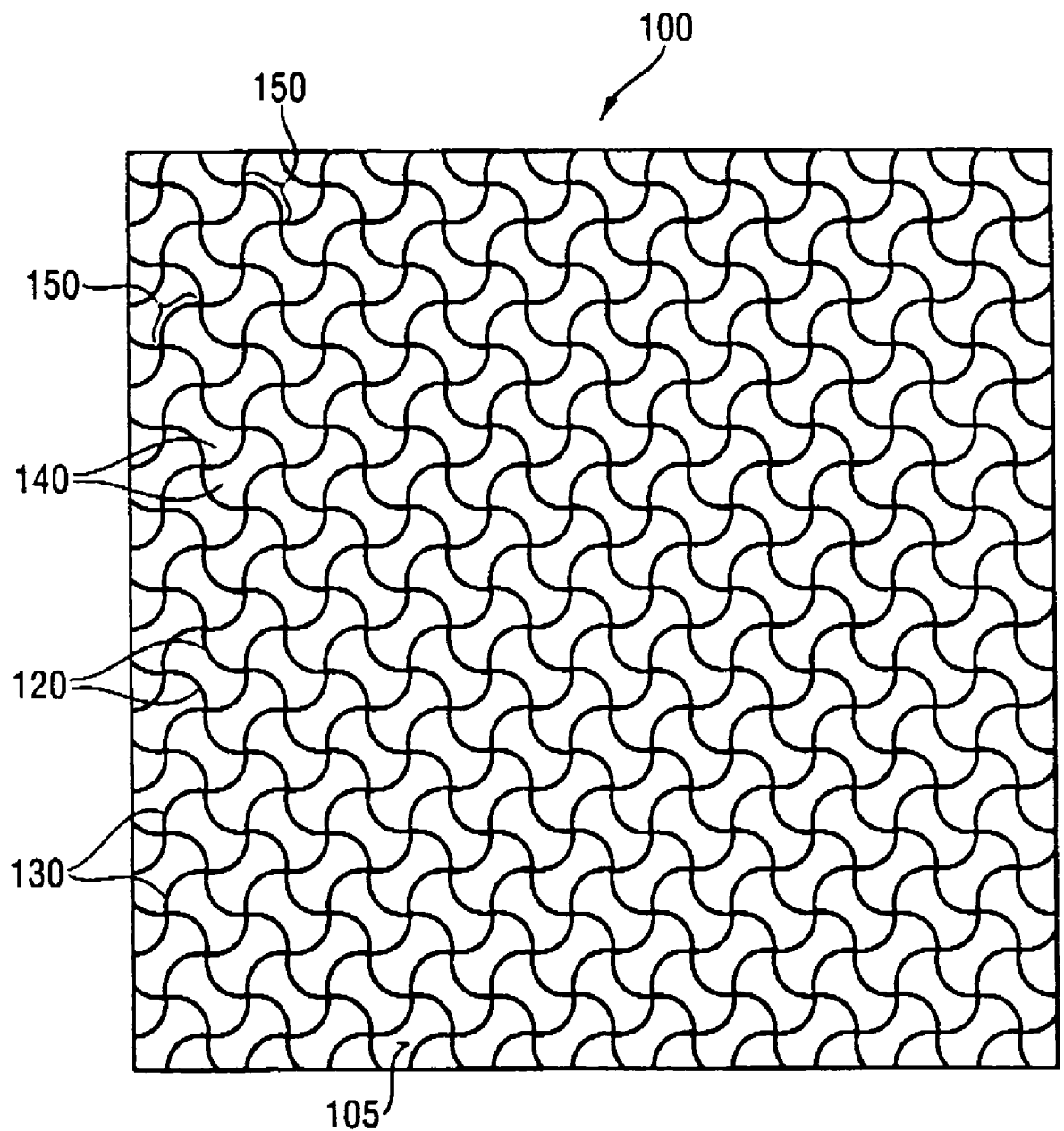
FIG. 6 is a plan view of another embodiment of a loop member of the present invention.

In a preferred embodiment, first plurality of non-intersecting continuous bond lines 120 and a second plurality of non-intersecting bond lines 130 are combined to form a pattern of intersecting bond lines that define tessellating pattern elements 140 having equal size and shape. One such pattern is shown in FIG. 6. The pattern of FIG. 6 is formed by the first and second plurality of non-intersecting bond lines (120, 130) each being a wave pattern having a constant pitch and amplitude. For each plurality of non-intersecting bond lines (120, 130), adjacent bond lines can be described as having equal pitch and amplitude but being 180 degrees out of phase. By choosing the spacing of bond lines within each plurality to be equal, and choosing the appropriate intersection points, the pattern can be made to comprise tessellating pattern elements 140, which can be described as "dog-bone" shaped.

As shown in FIG. 6, the tessellating shapes of pattern elements 140 can be of equal shape and size. However, in other embodiments, the pattern elements 140 can be non-tessellating, and can be of unequal shape and size. For example, by introducing a third plurality of non-intersecting bond lines, a pattern of three-sided pattern elements 140 having unequal size and shape can be achieved.

It is believed that a pattern comprising at least a first and second plurality of continuous, non-intersecting bond lines (120, 130), the resulting pattern elements 140 will always be such that they can be described as elements bounded by at least two sides intersecting in at least two intersection points. For example, the pattern element shown in FIG. 4 exhibits four sides comprised of line segments 150. The "corners" of the pattern element of FIG. 4 are the intersection points of a larger pattern of which the element of FIG. 4 is a part. Thus, if three pluralities of continuous, non-intersecting bond lines are used, the pattern would comprise three-sided pattern elements 140. If only a fist and second plurality of continuous, non-intersecting bond lines are used, but each plurality is directionally parallel to the other, the superposed, overlapping pattern formed can result in two-sided, "eye-shaped" pattern elements 140. In no case, however, would "one-sided" pattern elements be formed, i.e., circular pattern elements 140. Thus, pattern elements 140 can be described as being non-circular in shape.

Pre-bonded, carded nonwovens over-bonded with the pattern of FIG. 6 having a line width of 0.58 mm and about 3.2 pattern elements 140 per square centimeter have been found to produce excellent reliability when used as a loop fastener with hooks as known for such fasteners, for example, as used as a landing zone on disposable diapers. Without being bound by theory, it is believed that the increased reliability is achieved because by introducing bond lines 120, 130 having non-linear segments 150, each pattern element 140 has associated therewith more anchored fibers without a proportional increase in the percentage of overall bonded area. Anchored fibers are fibers having portions bonded, and thus secured within the nonwoven, or to a backing, for example, to provide structural integrity, and yet also having unbonded portions, which are portions available for hook engagement. More fibers are anchored in a pattern of the present invention due to the increased length of the non-linear segment per unit basis, compared to a straight line bond pattern and, therefore, results in more fibers available for reliable hook engagement.

The more fibers captured, or anchored, yet having portions exposed for hook engagement, the more reliable the nonwoven is as a female fastening component in a mechanical fastener. For this reason, the concept of "contour" is introduced. The "contour" of a bond pattern is defined as the total length of unbonded fiber/bonded fiber interface for a given area of a pattern. For example, for a square pattern element, the contour associated with the area of one element is the length of the perimeter of the unbonded element at the interface of the unbonded fibers to the bonded fibers, that is, at the "edge" of the bond line. By way of example, the pattern element 140 shown in FIG. 3 is bounded by line segments 150, each of which have a width 153 defining an inner line edge 151 and an outer edge 152 and represent an area of bonded fibers that are no longer available for hook engagement. For the single pattern element 140 shown in FIG. 3, the total length of the inner line edges 151 of each segment 150 forms the unbonded fiber/bonded fiber interface for the area of the pattern element, which is, by definition, the contour of pattern element 140. In a pattern of multiple pattern elements 140, each pattern element 140 has a contour, and the total contour can be expressed in terms of length/area, such as mm/cm2, for example. Because the contour represents a measure of the interface between unbonded regions of pattern elements 140 and bonded regions 150, it is an indicator of the amount of fibers anchored and yet available for engaging with a hook element. For this reason contour has been chosen as a useful measure of the inventive aspects of the present invention.

In prior art nonwoven loop fasteners, higher nonwoven integrity was achieved by adding bond lines, while attempting to balance the needs of web integrity with the need to have a certain minimum number of fibers available for hook engagement. However, the increase in linear bond lines simply results in a directly proportional increase in contour. That is, in prior art linear bond patterns an increase in bond area was gained by a directly proportional gain in the number of anchored fibers. But since the overall bond area increased, such an increase in linear bond lines simply resulted in a directly proportional loss in total fibers available for engaging. This technical contradiction has been solved by the pattern of the present invention. Specifically, by the pattern of the present invention, the number of fibers anchored can be increased by increasing the contour, while not directly proportionally increasing overall bond area that reduces the number of fibers available for engaging hook members.

This relationship of contour to total bond area can be illustrated with respect to a particular pattern, for example the tessellating pattern 110 shown in FIG. 6, by varying the amount of non-linearity, for example, by incrementally increasing the amplitude of the wave forms of the bond lines. Data showing the change in bond area and contour with increasing amplitude is shown in Table 1 below. In FIG. 6 the tessellating pattern comprises 3.2 pattern elements 140 per square centimeter, with each unbonded area separated from each adjacent unbonded area by a bond line 150 having a width of 0.58 mm. For comparison purposes, therefore, the data of Table 1 is produced based on patterns 110 normalized to 3.2 unbonded areas per square centimeter and a bond line width of 0.58 mm. These dimensions have been found to result in a female fastening component suitable for application in a disposable diaper, but are not considered limiting.

TABLE 1

Effect of Amplitude Change on Contour and Bond Area

| Sample No. | Amplitude (mm) | Contour (mm/cm$^2$) | Bond Area (%) |
|---|---|---|---|
| 1 (control) | 0 | 64.43 | 19.8 |
| 2 | 0.625 | 67.18 | 20.6 |
| 3 | 0.688 | 67.70 | 20.7 |
| 4 | 0.750 | 68.28 | 20.9 |
| 5 | 0.813 | 68.87 | 21.1 |
| 6 | 0.875 | 69.58 | 21.3 |
| 7 | 0.938 | 70.29 | 21.5 |
| 8 | 1.000 | 71.00 | 21.7 |
| 9 | 1.063 | 71.84 | 21.9 |
| 10 | 1.125 | 72.69 | 22.2 |
| 11 | 1.188 | 73.53 | 22.5 |
| 12 | 1.250 | 74.43 | 22.7 |
| 13 | 1.313 | 75.40 | 23.0 |
| 14 | 1.375 | 76.44 | 23.3 |
| 15 | 1.438 | 77.48 | 23.6 |
| 16 | 1.500 | 78.51 | 23.9 |
| 17 | 1.563 | 79.61 | 24.2 |
| 18 | 1.625 | 80.71 | 24.5 |
| 19 | 1.688 | 81.94 | 24.9 |
| 20 | 1.750 | 83.17 | 25.2 |

TABLE 1-continued

Effect of Amplitude Change on Contour and Bond Area

| Sample No. | Amplitude (mm) | Contour (mm/cm$^2$) | Bond Area (%) |
|---|---|---|---|
| 21 | 1.813 | 84.34 | 25.6 |
| 22 | 1.875 | 85.63 | 26.0 |
| 23 | 1.938 | 86.86 | 26.3 |
| 24 | 2.000 | 88.22 | 26.7 |

As shown in Table 1, a prior art pattern (Sample 1, labeled "control") consisting of straight lines (amplitude=0 mm) each having a width 0.58 mm and spaced apart to a dimension that results in 3.2 equally shaped and sized pattern elements per square centimeter results in an overall bond area of 19.8%. That is, in one square centimeter, 19.8% of the area comprises fibers that are bonded and therefore are unavailable for engaging with a hook member. Additionally, the contour is 64.43 mm/cm$^2$. Thus, for this pattern, there are 64.43 mm of unbonded fiber/bonded fiber interface per square centimeter, which is representative of the number of fibers anchored by bonding but otherwise available for hook engagement.

Figure 7:
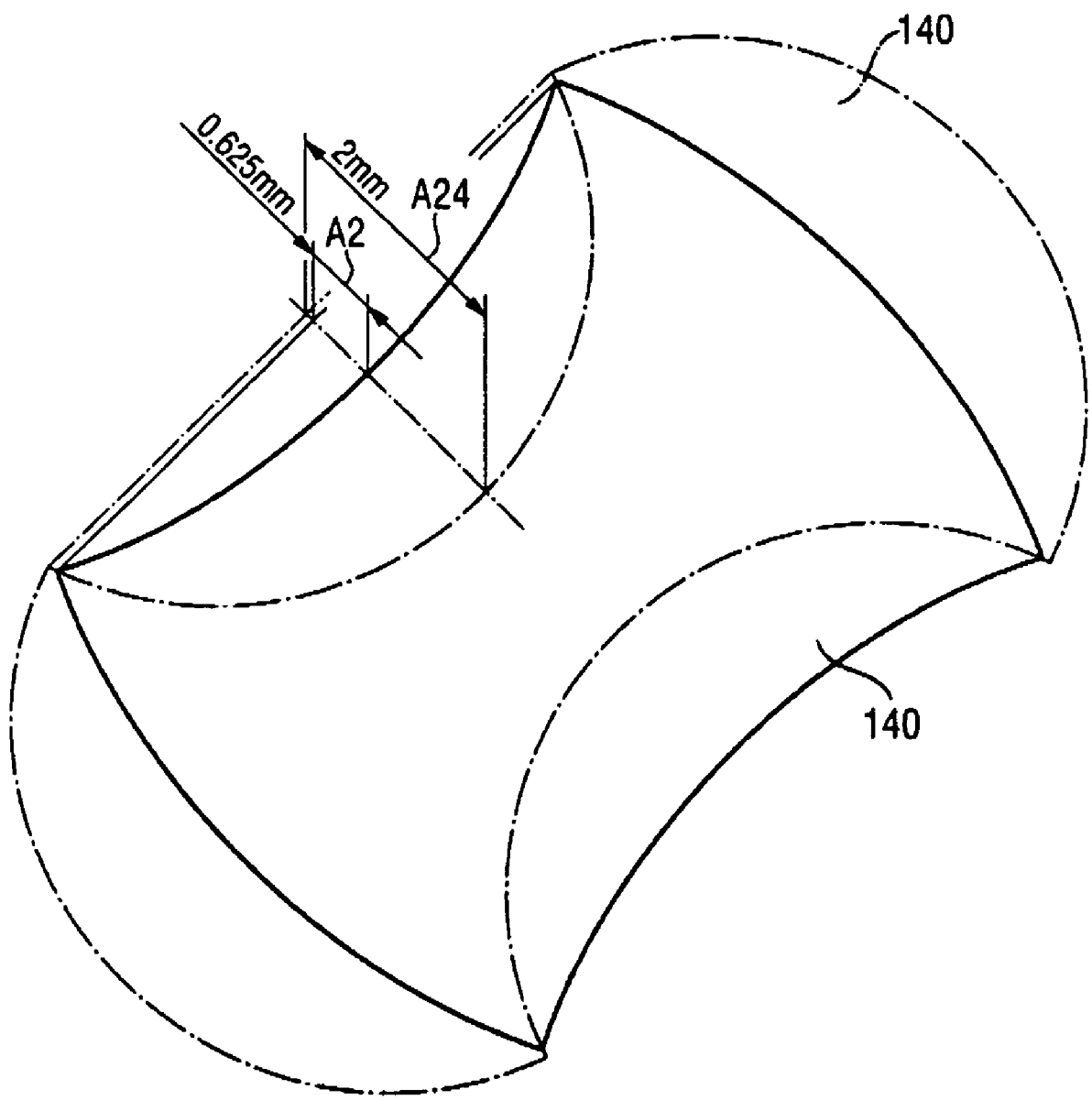
FIG. 7 is a diagram showing the amplitude for two variations of patterns of the type shown in FIG. 6.

Sample 2 of Table 1 is made by making each bond line wavy with each wave crest having a constant maximum amplitude of 0.625 mm. Amplitude is determined as shown in FIG. 7, and is the measure of the maximum deflection from linear at the crest of a wave of a bond line. For example, two representative pattern elements are shown superposed in FIG. 7. The first is the pattern corresponding to Sample 2, and has amplitude referenced as A2; the second corresponds to Sample 24, and has amplitude referenced as A24. In Sample 2 the overall bond area is 20.6% and the contour is 67.18 mm/cm$^2$. As shown in Table 1, the amplitude in each pattern is incrementally increased for each succeeding Sample, through Sample 24 which has an amplitude of 2 mm. In Sample 24, the overall bond area is 26.7%, and the contour is 88.22 mm/cm$^2$.

FIG. 8 shows a graph of the data in Table 1, in which the Total Bond Area (%) is shown as a solid line, and the Contour (mm/cm2) is shown as a broken line. Along the horizontal axis is Amplitude for each Sample from 1 to 24, and the vertical axis is evenly marked in increments of 10 from 0 to 100. As can be seen in the graph of FIG. 8, as the non-linearity of the bond lines increases, the contour increases at a faster rate than the overall bond area percentage. Thus, for a given increase in overall bond area per unit area, there is a correspondingly greater increase in the number of fibers anchored and available for more reliable hook engagement. This can be expressed as an increase in the ratio of contour to overall bond area with increasing non-linearity of the constituent bond lines. As the non-linearity of the pattern increases, the ratio of contour to overall bond area increases.

Thus, one way of describing the present invention is a bond pattern for a nonwoven web suitable for use as a loop member of a mechanical fastener, the bond pattern comprising intersecting bond lines having a uniform width and defining a number of bond pattern elements per unit area, wherein at least one of the bond lines is nonlinear, and wherein the ratio of contour to overall bonded area of the bond pattern is greater than a bond pattern comprising all straight lines having the same uniform line width and defining the same number of bond pattern elements per unit area.

Because there are more anchored fibers available for hook engagement, patterns of the present invention produce nonwoven loop fastener material having greater reliability as the female component of a mechanical fastener. This greater reliability is exhibited in both greater resistance to shear force without negatively impacting peel force, for example. In a disposable diaper, for example, a resistance to shear forces is very beneficial for maintaining proper fit on the wearer. By increasing the contour of the pattern elements 140 of the present invention, more fibers are anchored, which means any given hook is less likely to be disengaged by a sliding action when the fastener is subjected to shear forces (e.g., by sliding off the end of an unbonded fiber end).

The bond pattern 110 can be made by methods known in the art for imparting bond patterns to nonwoven materials, including by way of heat (thermal bonding), ultrasonic bonding, or by adhesive bonding. For example, patterned nip roller arrangements that utilize heat and/or pressure to impart a thermal bond pattern. Additionally, a gravure method using a patterned roller having raised pattern elements corresponding to a pattern as shown in FIG. 6 can be used with heat and/or pressure to impart an adhesive bond pattern 110. If the nonwoven web is elastic the web can be stretched prior to bonding, and allowed to relax to produce shirred fibers and higher loft loops, which can improve the chances for proper hook engagement.

Bond pattern 110 can be imparted to a nonwoven directly as a discrete web to consolidate it, or to impart an additional pattern to a web which has been consolidated, for example by pre-bonding of discrete thermal bonds. Bond pattern 110 can also be imparted in a process of bonding a nonwoven web to a backing material, such as a thermoplastic film. Additionally, the backing material can be elastic or comprise elastic components, and can be stretched prior to bonding a nonwoven material thereto. The loop fastener 100 can be made by bonding a nonwoven to an elastomeric backing film to form a stretch bonded laminate, as is known in the art. Once allowed to relax, the loose, unbonded fibers become shirred, thus providing for increased loft and better hook engagement.

In a preferred embodiment, bond lines 110 are produced by calendaring a nonwoven web and, optionally, a nonwoven web and a backing film, through the nip of a pair of complementary bonding rollers under relatively light web back tension. One or both of the rollers can be heated to achieve thermal bonding. One roller can comprise a raised pattern that imparts the bond pattern 110 to the nonwoven loop fastener 100, and the other roller can be a smooth anvil roller. Temperature, pressure, line speed, and web tension can each be adjusted by methods known in the art of thermal web bonding to achieve adequate bonding in the pattern 110 of the present invention. In addition to adequate bonding, the processing parameters can be adjusted to produce desired effects in the finished nonwoven web. For example, by adjusting web tension, it has been found that the finished caliper of the nonwoven web can be altered. It has been found, for example, that by minimizing back tension of the web going into the nip of the calendaring rollers the caliper of the calendared web(s) can be maintained, resulting in a beneficial three-dimensional effect of the finished nonwoven web. This three-dimensional effect produces beneficial texture and loft to the nonwoven web, both of which result in improved loop fastener performance.

While particular embodiments of the present invention have been illustrated and described, it would be obvious to those skilled in the art that various other combinations and modifications can be made without departing from the scope of the invention. It is therefore intended to cover in the appended claims all such combinations and modifications that are within the scope of this invention.

What is claimed is:

1. A fibrous web having a pattern of intersecting bond lines, said pattern comprising a first plurality of linear non-intersecting continuous bond lines and a second plurality of non-linear non-intersecting continuous bond lines, each linear non-intersecting continuous bond line of said first plurality intersecting each non-linear non-intersecting continuous bond line of said second plurality, said pattern of intersecting bond lines defining unbonded pattern elements, each of said pattern elements being bounded by two linear segments and two non-linear segments.

2. The web of claim 1 wherein each bond line in said first plurality of linear non-intersecting continuous bond lines is disposed at a constant equal distance from adjacent bond lines.

3. The web of claim 1, wherein each bond line in said second plurality of non-linear non-intersecting continuous bond lines defines a wave pattern.

4. The web of claim 3, wherein in said second plurality of non-linear non-intersecting continuous bond lines adjacent bond lines are 180 degrees out of phase.

5. The web of claim 1, wherein said nonwoven web is chosen from the group consisting of: spunbond webs, meltblown webs, carded webs, and hydroentangled webs.

6. The web of claim 1, wherein said nonwoven web is bonded to a backing member.

7. The web of claim 6, wherein said backing member is elastomeric, and said nonwoven web is shirred.

8. The web of claim 1, wherein the fibrous web is a nonwoven web.

* * * * *

UNITED STATES PATENT AND TRADEMARK OFFICE
CERTIFICATE OF CORRECTION

| | | |
|---|---|---|
| PATENT NO. | : 7,805,818 B2 | Page 1 of 1 |
| APPLICATION NO. | : 10/781613 | |
| DATED | : October 5, 2010 | |
| INVENTOR(S) | : Horn et al. | |

It is certified that error appears in the above-identified patent and that said Letters Patent is hereby corrected as shown below:

Column 11
Line 21, delete "fist" and insert --first--.

Signed and Sealed this
Sixteenth Day of August, 2011

David J. Kappos
*Director of the United States Patent and Trademark Office*